(12) United States Patent
Jung et al.

(10) Patent No.: US 8,404,282 B2
(45) Date of Patent: Mar. 26, 2013

(54) COMPOSITIONS FOR SUPPRESSING OBESITY

(75) Inventors: Yang Sam Jung, Yeonje-Gu (KR); Ki Hyeon Yoon, Mapo-Gu (KR); Soon Shik Shin, Dongrae-Gu (KR)

(73) Assignee: Dong-Eui Educational Foundation, Busanjin-Gu (KR)

( * ) Notice: Subject to any disclaimer, the term of this patent is extended or adjusted under 35 U.S.C. 154(b) by 337 days.

(21) Appl. No.: 12/596,018

(22) PCT Filed: May 1, 2007

(86) PCT No.: PCT/KR2007/002135
§ 371 (c)(1),
(2), (4) Date: Apr. 20, 2010

(87) PCT Pub. No.: WO2008/146955
PCT Pub. Date: Dec. 4, 2008

(65) Prior Publication Data
US 2010/0215688 A1    Aug. 26, 2010

(30) Foreign Application Priority Data
Apr. 19, 2007 (KR) .......... 10-2007-0038134

(51) Int. Cl.
*A61K 36/00* (2006.01)
*A61K 36/708* (2006.01)
*A61K 36/02* (2006.01)

(52) U.S. Cl. .............. 424/725; 424/195.17

(58) Field of Classification Search .............. None
See application file for complete search history.

(56) References Cited

U.S. PATENT DOCUMENTS

2004/0071799 A1* 4/2004 Xu et al. ............ 424/756
2004/0265398 A1* 12/2004 Fleischner .......... 424/725

FOREIGN PATENT DOCUMENTS

| CN | 1839978 A | | 10/2006 |
|---|---|---|---|
| JP | 08-191668 | | 7/1996 |
| JP | 2000-072642 | | 3/2000 |
| KR | 2003058906 A | * | 7/2003 |
| KR | 10-2004-0107544 | | 12/2004 |
| KR | 10-2005-0022951 | | 3/2005 |
| KR | 10-2005-0120302 | | 12/2005 |
| KR | 10-2005-0053069 | | 12/2006 |

* cited by examiner

*Primary Examiner* — Qiuwen Mi
(74) *Attorney, Agent, or Firm* — Dickstein Shapiro LLP (57) ABSTRACT

Disclosed herein is a composition for suppressing and preventing obesity and related adult diseases, comprising Herba Ephedrae and Thallus Laminariae seu Eckloniae, or comprising Herba Ephedrae, Thallus Laminariae seu Eckloniae and Radix et Rhizoma Rhei.

2 Claims, 8 Drawing Sheets

| mice\days | C57BL/6J | vehicle | GGEx0012 | GGEx0013 | GGEx0014 | GGEx0015 | GGEx0016 | GGEx0017 | GGEx0018 | reductil |
|---|---|---|---|---|---|---|---|---|---|---|
| 5 | 0.3±0.39 | 1.62±0.23** | 0.74±0.67* | -0.38±1.58 | -0.12±0.54 | -0.64±0.48 | -1.42±0.9 | 0.46±0.84 | -0.78±1.09 | 1.22±0.74** |
| 8 | 0.22±0.45 | 2.18±0.69*** | 0.6±1.15* | -0.68±1.79 | -1.28±0.88 | -1.62±1.96 | -2.86±0.51 | -0.2±0.94 | -1.64±1.33 | 2.08±0.94*** |
| 12 | 0.96±0.69 | 4.26±0.77** | 1.39±1.46 | 0.74±1.75 | 0.6±1.17 | -0.72±2.08 | -1.08±0.84 | 1.36±0.85* | -0.36±1.41 | 2.6±0.73** |
| 15 | 0.48±0.32 | 4.4±0.8** | 1.64±1.56 | -0.02±1.73 | -0.98±1.89 | -1.24±1.27 | -0.68±0.73 | 1.8±0.86* | 0.04±1.44 | 3.72±0.65*** |
| 19 | 1.2±0.62 | 5.64±1.34*** | 2.93±1.77 | 1.18±2.48 | 0.32±2.62 | -0.46±1.58 | -0.08±0.87 | 2.88±1.26 | 1.02±1.45 | 4.62±0.99*** |
| 22 | 1.5±0.6 | 6.24±1.52*** | 3.95±1.84 | 2.96±2.3 | 1.03±2.09 | 0.29±1.87 | 0.64±0.93 | 3.46±1.3 | 1.6±1.47 | 5.74±0.79*** |
| 26 | 2±0.7 | 7.66±1.41*** | 4.34±2.25 | 2.58±2.46 | 2.04±2.34 | 0.92±1.23* | 2.12±1.24 | 4.84±1.11* | 2.82±1.29 | 5.22±0.77* |
| 29 | 2.48±0.69 | 8.38±1.49*** | 5.18±2.04 | 4.16±2.29 | 3.08±2.22 | 1.56±1.13 | 2.26±1.02 | 5.16±1.03** | 2.94±1.01 | 7.04±0.52# |
| 33 | 2.88±0.49 | 9.58±1.32* | 5.62±2.37 | 5.58±2.1 | 4.28±2.5 | 2.92±0.74 | 2.64±1.1 | 5.28±0.78* | 3.4±1.21 | 7.82±0.8*** |
| 36 | 3±0.61 | 10.34±1.24# | 6.8±2.56 | 6.56±1.95 | 5.5±2.26 | 4.06±1.21 | 3.86±0.91 | 6.36±0.69* | 4.4±1.13 | 8.16±1.08*** |
| 40 | 3.92±0.85 | 11.42±1.45*** | 7.83±2.64 | 6.98±1.89 | 5.84±2.29 | 4.84±1.03 | 4.38±0.98 | 6.88±0.73* | 5.06±1.34 | 8.9±1.14** |
| 43 | 3.56±0.99 | 12.3±1.43*** | 8.4±2.92 | 7.86±1.7 | 7.5±2.54 | 6.04±1.3 | 4.72±1.03 | 7.56±0.74 | 5.9±1.53 | 9.66±1.11** |
| 47 | 3.62±0.83 | 12.34±1.61*** | 8.83±2.83 | 8.28±1.67* | 8.22±2.41 | 6.54±1.46 | 5.52±1.09 | 7.6±0.96* | 5.9±1.24 | 10.56±1.16*** |
| 50 | 3.64±1.07 | 13.26±1.56* | 9.96±3.04 | 8.72±1.72 | 8.42±1.95 | 6.92±1.83 | 5.98±0.68 | 8.3±0.76* | 6.7±1.15 | 10.76±1.31*** |
| 54 | 4.12±0.88 | 14±1.51*** | 10.62±2.91 | 9.12±1.65 | 8.98±2.17 | 6.9±1.76 | 6.56±0.91 | 9.04±0.75 | 7.5±1.62 | 11.3±1.34** |
| 57 | 3.86±0.84 | 13.42±1.99*** | 11.24±3.11* | 10.02±1.55* | 9.78±2.39 | 7.8±1.11 | 6.82±0.79 | 9.24±0.77* | 7.22±1.72 | 12.26±1.5** |
| 61 | 4.34±0.94 | 14.82±1.26# | 11.38±3.1 | 10.32±1.51* | 10.66±2.23 | 8.1±1.28 | 7.34±0.76 | 9.38±1.15 | 7.96±1.55 | 13.62±1.93*** |
| 64 | 4.68±0.81 | 15.34±1.58*** | 11.92±3.05 | 11.06±1.27 | 11±2.21 | 8.3±1.2 | 7.92±0.29 | 10.34±0.88 | 8.6±1.59 | 12.9±1.69** |
| 68 | 5.08±0.75 | 16.44±1.87*** | 12.6±2.99 | 11.62±1.48 | 11.26±1.83 | 8.92±1.59 | 8.38±0.54 | 11.3±0.78 | 9.64±1.69 | 14.12±1.84** |
| 71 | 5.12±1 | 16.42±1.67*** | 12.46±3.26 | 12.36±1.3** | 12.32±2* | 9.68±1.47 | 8.48±0.43 | 11.38±1.09* | 9.3±1.53 | 13.58±2.18*** |
| 75 | 5.46±0.78 | 16.54±1.9*** | 13.12±3.36 | 13.5±1.06** | 13.48±1.88* | 10.2±1.74 | 9.44±0.72 | 12.7±1.09* | 9.74±1.76 | 14.86±1.85** |
| 78 | 5.92±0.75 | 16.24±2.09*** | 13.74±3.54* | 13.5±1.16** | 12.82±1.91** | 10.08±2.01 | 8.96±0.86 | 11.76±1.17 | 9.24±1.82 | 14.04±2.03** |

All values are expressed as means±SD. *p<0.05; p<0.01; *p<0.001; #p<0.0001 compared with respective GGEx0018 groups.

FIG. 3

All values are expressed as means ±SD. *p<0.05; **p<0.01 compared with respective GGEx0018 groups

FIG. 4

All values are expressed as means ±SD. *p<0.05; **p<0.01 compared with respective GGEx0018 groups

FIG. 5

All values are expressed as means ±SD. *p<0.05 compared with respective GGEx0018 groups

FIG. 6

All values are expressed as means ±SD. *p<0.05; **p<0.01 compared with respective GGEx0018 groups.

Histological analyses of hepatic lipid accumulation in genetically obese ob/ob mice
Wild-type C57BL/6 and od/ob mice received a chow diet or the same chow diet
supplemented with GGEx or reductil for 8 weeks
0, no lesion; 1, mild; 2, moderate; 3, severe; 4, very severe
* $p<0.01$, ** $p<0.005$ Significantly different from Vehicle. V, vehicle

COMPOSITIONS FOR SUPPRESSING OBESITY

TECHNICAL FIELD

The present invention relates to a composition for suppressing obesity comprising Herba Ephedrae and Thallus Laminariae seu Eckloniae, or comprising Herba Ephedrae, Thallus Laminariae seu Eckloniae and Radix et Rhizoma Rhei.

BACKGROUND ART

Obesity is defined as the excess accumulation of body fat to an extent that is harmful to health (Edited by Per BjInternational Textbook of Obesity. West Sussex: John Wiley & Sons. Ltd., 2001, ISBN 0-471-98870-7, 3-22.). Obesity was considered a symbol of wealth in the past. Today, however, excess body weight has been proven to be a risk factor for various pathological conditions, such as diabetes and arteriosclerosis, leading to increased morbidity and mortality and causing social and psychological problems. Thus, obesity is now regarded as a chronic disease that should be treated (Manson J E, Willet W C, Stampfer M J, Colditz G A, Hunter D J, Hankinson S E, Hennekens C H, Speizer F E. Body weight and mortality among women. N Eng J Med 1995, 333:677-685; Hubert H B, Feinleib M, McNamara P M, Castelli W P. Obesity as an independent risk factor for cardiovascular disease: a 26-year follow-up of participants in the Framingham Heart Study. Circulation 1983, 67:968-977; Pi-Sunyer FX. Medical hazard of obesity. Ann Intern Med 1993, 119:655-660; Huang Z, Willett W C, Manson J E, Rosner B, Stampfer M J, Speizer F E, Colditz G A. Body weight, weight change, and risk for hypertension in women. Ann Intern Med 1998, 128:81-88; Colditz G A, Willett W C, Stampfer M J, Manson J E, Hennekens C H, Arky R A, Speizer F E. Weight as a risk factor for clinical diabetes in women. Am J Epidemiol 1990, 132:501-513).

According to the World Health Organization (WHO), more than 1.2 billion people worldwide are classified as being overweight or obese. In 2000, about 65% of adult Americans were estimated to be overweight (World Health Organization, Obesity: Preventing and Managing the Global Epidemic Report of a WHO Consultation on Obesity, 1997 Jun: 32-5; Flegal K M, Carroll M D, Ogden C L, Johnson C L, Prevalence and trends in obesity among US adults, 1999-2000 JAMA 2002, 288:1723-1727). Also, about 300,000 deaths per year are associated with obesity in the US (Allison D B, Fontaine K R, Manson J E, Stevens J, VanItallie T B, Annual Deaths Attributable to Obesity in the United States, JAMA 1999, 282:1530-1538).

Excess weight or obesity contributes significantly to numerous diseases. Around the world, about 80% of diabetes cases and 21% of cardiovascular disease are attributable to excess weight. As well, weight is associated both directly and indirectly with various types of cancer, including cancer of the uterus, kidneys and breasts. People who are overweight or obese have a greater likelihood of developing sleep apnea, osteoarthritis, cholelithiasis, and others (Stein C J, Colditz G A, The epidemic of obesity, J Clin Endocrinol Metab 2004, 89:2522-2525; Kopelman P G, Obesity as a medical problem, Nature 2000 Apr. 6, 404(6778):635-43). As described above, obesity reduces life expectancy and threatens health.

Obesity imposes a large economic burden on societies. Americans gained an average weight of about 10 pounds (4.5 kg) during the 1990s. Airlines spent $275 million to burn 350 million more gallons of fuel in 2000 to carry the extra weight (Dannenberg A L, Burton D C, Jackson R J, Economic and environmental costs of obesity: the impact on airlines, AM J Prev Med, 2004 Oct. 27(3): 264). The direct and indirect health care costs associated with obesity have been estimated to amount to about $117 billion in the US every year. In South Korea, according to data from the 2001 National Health & Nutrition Survey, the social and economic costs of obesity account for 1001.7 billion Won. This, which is the sum of medical care costs of obesity and the value of lost and reduced productivity resulting from premature death and illness, accounts for about 5% of total national medical care expenditures (the 2001 Korean National Health & Nutrition Survey conducted by the Korea Institute for Health and Social Affairs under the Ministry of Health and Welfare). In 2000, the global market for obesity drugs was estimated at about $1.3 billion in 2000. This market is expected to reach $8 billion in 2010.

Obesity is seldom curable because it is caused not by one factor but by a complex interplay of several hereditary, environmental, social and psychological factors. Obesity occurs when energy intake exceeds energy expenditure. Thus, obesity arising from energy imbalance can be resolved by reducing caloric intake and increasing caloric expenditure. At present, there are two major options for obesity treatment: one is to make lifestyle changes through dietary therapy, physical activity, behavior therapy, and the like, and the other includes drug therapy and surgery.

Patients should definitely make efforts to change their lifestyle before starting drug treatment or having weight loss surgery. However, is not easy to change one's lifestyle, and moreover, merely making a lifestyle change without using drugs is of limited effectiveness for losing weight. Thus, in many cases, weight loss can be achieved more effectively by making lifestyle changes along with drug therapy.

At present, sibutramine and orlistat are the only medications that have been approved by the US Food & Drug Administration (FDA) for use in the treatment of obesity. Sibutramine (Reductil®) is a serotonin-norepinephrine reuptake inhibitor, and orlistat (Xenical®) inhibits gastric and pancreatic lipases (Yanovski S Z, Yanovski J A, Obesity, N Engl J Med 2002, 346:591-602).

However, the two obesity medications have not been widely used due to some limitations. Common side effects of sibutramine include increased blood pressure, insomnia, dry mouth and dizziness. People having cardiovascular diseases or poorly controlled high blood pressure should not take sibutramine (H S Park, Sibutramine, The Korean Journal of Obesity 1998, 7(4):270-3).

Orlistat also has limitations in use for obesity treatment. Common side effects of orlistat include diarrhea, oily stools and fecal incontinence. As well, orlistat has not shown great therapeutic effects in people, like Koreans, having a low fat diet compared to Westerners (S M Kim, Study on Orlistat, The Korean Journal of Obesity 1998, 7(4): 287-92). The two obesity medications need to be studied with an eye to their long-term safety.

Due to the drawbacks of conventional medications developed for obesity treatment, there is an urgent need for the development of a medication that is highly effective for losing weight and has few side effects because it has a novel action mechanism. In this regard, the inventors of this application assumed that Chinese herbal medicines have potential as an alternative to conventional medications for obesity, and have conducted intensive and thorough research to evaluate their effectiveness, resulting in the finding that a composition comprising Herba Ephedrae and Thallus Laminariae seu Eckloniae or comprising Herba Ephedrae, Thallus Laminariae seu Eckloniae and Radix et Rhizoma Rhei has an effect of suppressing an increase in body weight, leading to the present invention.

DISCLOSURE

Technical Problem

It is therefore an object of the present invention to provide a composition for suppressing obesity comprising Herba Ephedrae and Thallus Laminariae seu Eckloniae, or comprising Herba Ephedrae, Thallus Laminariae seu Eckloniae and Radix et Rhizoma Rhei.

It is another object of the present invention to provide a pharmaceutical composition for suppressing obesity or a health food composition for suppressing obesity, comprising the composition for suppressing obesity.

It is a further object of the present invention to provide a method of preparing the composition for suppressing obesity.

DESCRIPTION OF DRAWINGS

FIG. 2 is a table showing the average daily weight gains of control obese mice and mice dosed with GGEx0012, GGEx0013, GGEx0014, GGEx0015, GGEx0017 and Reductil®;

BEST MODE

In one aspect, the present invention relates to a composition for suppressing obesity, comprising Herba Ephedrae and Thallus Laminariae seu Eckloniae, or comprising Herbs Ephedrae, Thallus Laminariae seu Eckloniae and Radix et Rhizome Rhei.

Herba Ephedrae has diaphoretic, antipyretic, analgesic, antitussive, expectorant, blood pressure control (raising or lowering), diuretic, renal function improving, anti-inflammatory, and anti-allergic actions. It has been used to relieve or cure coughing, upper respiratory infections, pneumonia, bronchitis, bronchial asthma, whooping cough, hypotension, heart diseases, diseases of skin and mucous membranes, nephritis and swelling, diseases of joints and muscles, and diarrhea. Herba Ephedrae has been used to prepare a traditional Ma Huang Tang (Ephedrae Herba Decoction), and has been used to dispel the common cold, having wind-cold syndromes manifested as headaches, fever, aversion to wind and lack of sweat. Also, it has been used to relieve osteoarthritis, lower back pain and rheumatoid arthritis with fever at acute phases, and asthma (Wang Ben Xiang, Editor-in-Chief, Modern Pharmacology and Clinic of Chinese Traditional medicine, Tianjin: Tianjin Science & Technology Translation & Publishing Co., 2004, ISBN 7-5433-1801-6, 1448-1460; Wang Yu Sheng, Deng Won Long, Xue Chun Sheng, Editors-in-Chief, Pharmacology and Application of Chinese Traditional. Medicine ($2^{nd}$ Edition), Beijing: People's Medical Publishing House, 2000, ISBN 7-117-03057-7/R3058, 1105-1119).

Thallus Laminariae seu Eckloniae has thyroid function-improving, blood pressure-lowering, anticoagulant, cardiotonic, body fat-improving, arteriosclerosis-preventing and suppressing, and anticancer actions. It has been used to resolve goiter, hypertension, diabetes, cerebrovascular diseases, epidemic hemorrhagic fever, cataract, and dry cough (Wang Ben Xiang, Editor-in-Chief, Modern Pharmacology and Clinic of Chinese Traditional medicine, Tianjin: Tianjin Science & Technology Translation & Publishing Co., 2004, ISBN 7-5433-1801-6, 910-914; Wang Yu Sheng, Deng Wen Long, Xue Chun Sheng, Editors-in-Chief, Pharmacology and Application of Chinese Traditional Medicine ($2^{nd}$ Edition), Beijing: People's Medical Publishing Rouse, 2000, ISBN 7-117-03057-7/R3058, 684-688).

Radix et Rhizoma Rhei has cathartic and hepatic protection actions, promotes pancreatic juice and bile secretion, has antimicrobial, antiviral, antipyretic and anti-inflammatory actions, lowers blood pressure, improves lipid metabolism, and has hemostatic and immunoenhancing actions. It has been used to resolve acute infectious fever and constipation, epidemic hemorrhagic fever, acute intestinal obstruction, various acute intoxications due to agricultural, chemicals, acute pancreatitis accompanying high fever, acute cholecystitis, upper digestive bleeding, chronic renal failure, acute hemorrhagic necrotic enteritis, diabetic kidney diseases, digestive disorders and constipation, chronic gastritis and digestive ulcers, hyperlipidemia, and pregnant hypertension (Wang Ben Xiang, Editor-in-Chief, Modern Pharmacology and Clinic of Chinese Traditional medicine, Tianjin: Tianjin Science & Technology Translation & Publishing Co., 2004, ISBN 7-5433-1801-6, 115-1237 Wang Yu Sheng, Deng Wen Long, Xue Chun Sheng, Editors-in-Chief, Pharmacology and Application of Chinese Traditional Medicine ($2^{nd}$ Edition), Beijing: People's Medical Publishing House, 2000, ISBN 7-117-03057-7/R3058, 70-80).

Each of the Herba Ephedrae, Thallus Laminariae seu Eckloniae and Radix et Rhizoma Rhei of the present invention has a low anti-obesity effect by itself. The anti-obesity effects of the ingredients are synergized when Herba Ephedrae is combined either with Thallus Laminariae seu Eckloniae or with Thallus Laminariae seu Eckloniae and Radix et Rhizoma Rhei. Thus, the combinations have anti-obesity effects superior to the ingredients when used individually. In addition to having synergic effect in suppressing obesity, Thallus Laminariae seu Eckloniae minimizes the side effects of Herba Ephedrae and Radix et Rhizoma Rhei, for example, side effects caused by ephedrine alkaloids, which are the main components of Herba Ephedrae, or side effects caused by sennosides, which are the main components of Radix et Rhizoma Rhei.

The composition comprising Herba Ephedrae and Thallus Laminariae seu Eckloniae according to the present invention comprises Herba Ephedrae and Thallus Laminariae seu Eckloniae at a ratio of 30-50:50-70 weight percent, and preferably at a ratio of 35-45:55-65 weight percent. The composition comprising Herba Ephedrae, Thallus Laminariae seu Eckloniae and Radix et Rhizoma Rhei according to the present invention comprises Herbs Ephedrae, Thallus Laminariae seu Eckloniae and Radix et Rhizoma. Rhei at a ratio of 10-50:20-50:20-50 weight percent, and preferably at a ratio of 30-50:20-40:20-40 weight percent. These combinations of the ingredients were determined by the inventors of this application taking into account effective doses, side effects and other factors of the herbal ingredients. If the herbal ingredients are not present within these weight ratios, their pharmaceutical effects may decrease, or side effects may occur.

The compositions according to the present invention are prepared as follows.

For the composition comprising Herba Ephedrae and Thallus Laminariae seu Eckloniae, crude herbs of Herba Ephedrae and Thallus Laminariae seu Eckloniae are washed with water and dried in the shade. The dried herbs are placed in a reflux extractor or an electronic herbal extractor, and ten volumes of distilled water are added. The herbs are heated for 22 hours after the water is boiled. The heat-water extract is cooled at room temperature and passed through a filter paper under pressure. The filtrate is concentrated using a vacuum evaporator and then dried using a freeze dryer to yield the desired composition of the present invention.

For the composition comprising the three herbal ingredients as described above, crude herbs of Herba Ephedrae, Thallus Laminariae seu Eckloniae and Radix et Rhizoma Rhei are washed with water and dried in the shade. The dried herbs of Herba Ephedrae and Thallus Laminariae seu Eckloniae are ground and placed in a reflux extractor, and ten volumes of distilled water are added. The herbs are heated for 21 hours and 50 minutes after the water is boiled. The dried herb of Radix et Rhizoma Rhei is ground and immersed in ten volumes of distilled water for 21 hours and 50 minutes. Then, the immersion solution of Radix et Rhizoma Rhei is added to the herbal extract of Herba Ephedrae and Thallus Laminariae seu Eckloniae, and the mixture is further heat-water extracted for about 10 minutes. The resulting heat-water extract is cooled at room temperature and passed through a filter paper under pressure. The filtrate is concentrated using a vacuum evaporator and then dried using a freeze dryer to yield the desired composition of the present invention.

Figure 3:
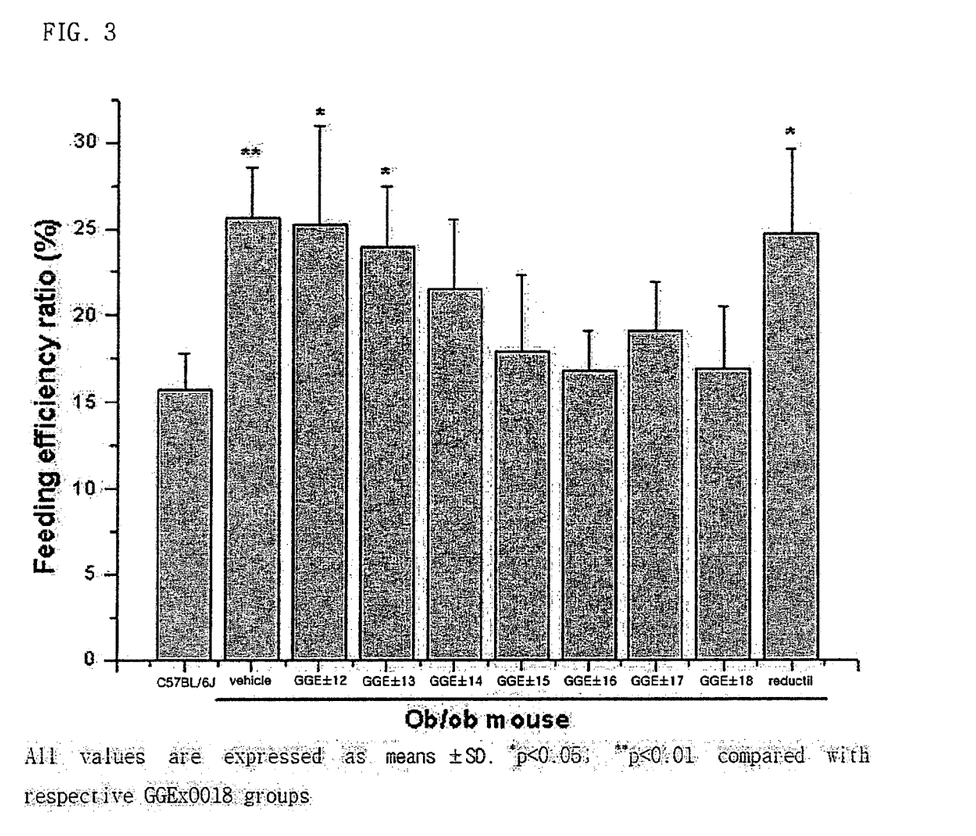
FIG. 3 is a graph showing the feeding efficiency ratios (FER) of control obese mice and mice dosed with GGEx0012, GGEx0013, GGEx0014, GGEx0015, GGEx0017 and Reductil®, wherein FER was calculated as grams of feed consumed per gram of weight gain.

Compared to the cases when Herba Ephedrae, Thallus Laminariae seu Eckloniae and Radix et Rhizoma Rhei were individually administered, Herba Ephedrae was administered along with Radix et Rhizoma Rhei, and the appetite suppressor Reductil® was administered, the composition comprising Herba Ephedrae and Thallus Laminariae seu Eckloniae, or the composition comprising Herba Ephedrae, Thallus Laminariae seu Eckloniae and Radix et Rhizoma Rhei further reduced weight gain in mice (FIGS. 1 and 2), and showed lower feeding efficiency rates (FIG. 3). These results indicate that the present compositions are useful for suppressing obesity. Also, the administration of the present compositions into mice resulted in a marked decrease in the serum levels of triglyceride, leptin and glutamic oxaloacetic transaminase (GOT) (FIGS. 4 to 6) and lower fat accumulation in liver tissues (FIGS. 7 and 8) compared to other treatment groups.

Thus, the present compositions may be useful for effectively suppressing obesity in mammalian animals, including humans, and may be useful for preventing various adult diseases caused by obesity, including myocardial infarction.

In addition to the herbal mixture, the present composition may include one or more effective ingredients having an identical or similar function. The present composition may be administered orally or parenterally in a general medicament form. That is, the present composition may be formulated into various pharmaceutical dosage forms for oral and parenteral administration upon clinical application. A formulation may be prepared with generally used diluents or excipients, such as fillers, thickeners, binders, humectants, disintegrators and surfactants. Solid formulations for oral administration may include tablets, pills, powders, granules and capsules. Also, the solid formulations may include, in addition to a simple excipient, a lubricant such as magnesium stearate or talc. Liquid formulations for oral administration may include suspensions, internal solutions, emulsions and syrups. The liquid formulations may include, in addition to commonly used simple diluents such as water and liquid paraffin, various excipients which are exemplified by humectants, sweeteners, aromatics and preservatives. Formulations for parenteral administration may include sterile aqueous solutions, non-aqueous solutions, suspensions, emulsions, lyophilized preparations, and suppositories. Non-aqueous solutions and suspensions may be prepared with propylene glycol, polyethylene glycol, vegetable oils such as olive oil, and injectable esters such as ethyl oleate. As a base of suppositories, witepsol, macrogol, tween 61, cacao oil, laurin oil and glycerinated gelatin may be used.

The unit dose may contain, for example, one, two, three or four individual doses, or one half, one third or one quarter of an individual dose. An individual dose preferably contains the amount of an effective drug which is given in one administration, and is usually all, one half, one third or one quarter of the daily dose. The present composition may be administered in an effective dose of 100 to 300 mg/kg, and preferably 140 to 270 mg/kg, once to six times per day.

When the present composition was administered orally to rats to evaluate its toxicity, it showed a 50% lethal dose (LD50) of 1 g/kg or higher, indicating that the present composition is safe.

The present composition may be used to suppress obesity either singly or in combination with surgery, radiotherapy, hormone therapy, chemical therapy or a biological response modifier.

The present composition may be added to health food in order to suppress obesity. When the present composition is used as a food additive, it may be added as it is or in combination with other food or food ingredients, and may be suitably used according to a general method. The amounts of effective ingredients may be properly determined depending on the intended use (preventive, health or therapeutic purposes). For the preparation of food or beverages, the present composition is typically added in an amount of 15 wt % or less, and preferably 10 wt % or less, based on the total weight of raw materials used. However, when consumed for a long period of time for health and sanitary purposes or health control, the present composition may be used in an amount lower than the above range. Also, it is apparent that the present composition can be used in an amount higher than the above range because the effective ingredients have no safety risk.

The type of food is not particularly limited. Examples of food to which the present composition can be added include meats, sausages, breads, chocolates, candies, snacks, confectionaries, pizza, instant noodles, other noodles, gum, dairy products including ice cream, various soups, beverages, teas, drinks, alcoholic beverages and vitamin complexes, as well as all traditional health foods.

A health food composition according to the present invention may additionally contain various sweeteners or natural carbohydrates, like general beverages. The natural carbohydrates include monosaccharides, such as glucose and fructose, disaccharides such as maltose and sucrose, and polysaccharides, such as dextrin and cyclodextrin. As the sweeteners, natural sweeteners or synthetic sweetening agents, such as saccharin or aspartame, may be used. The natural carbohydrates are used in an amount of about 0.01-0.4 g, and preferably about 0.02-0.03 g, based on 100 ml of the composition.

In addition, the present composition may contain various nutrients, vitamins, electrolytes, flavors, coloring agents, pectic acid and salts thereof, alginic acid and salts thereof, organic acids, protective colloidal thickeners, pH control agents, stabilizers, preservatives, glycerin, alcohol, carbonating agents for use in carbonated beverages, and the like. Further, the present composition may contain fruit flesh for preparing natural fruit juice, fruit juice beverages and vegetable beverages. Such ingredients may be used individually or in combination. Although the amount of such additives is not critical to the present invention, it is generally selected in the range of 0.01-0.1 parts by weight based on 100 parts by weight of the present composition.

MODE FOR INVENTION

A better understanding of the present invention may be obtained through the following examples which are set forth to illustrate, but are not to be construed as the limit of the present invention.

Example 1

Preparation of Compositions and Comparative Controls 1-1. Preparation of Gyeongshin-gangjee-hwan (GGEx) 0012 (GGEx0012)

Crude herbs of Herba Ephedrae were ground to a size of 200 mesh. 500 g of the powder and 5000 cc of water were added to an electronic herbal extractor, boiled at 95° C. for 22 hrs, and filtered. The filtrate was freeze-dried in an Ilshin Programmable Freeze Dryer (Ilshin Lab Co. Ltd., South Korea) in a vacuum of 5 mTorr for 48 hrs, in which the shelf temperature was raised to 40° C., while the condenser temperature remained at −70° C.

1-2. Preparation of GGEx0013

Crude herbs of Radix et Rhizoma Rhei were ground to a size of 200 mesh. 500 g of the powder was immersed in 5000 cc of water for 21 hrs and 50 min. The immersion solution containing the herbal powder was added to an electronic herbal extractor, boiled for 10 min, and filtrated. The filtrate was freeze-dried in an Ilshin Programmable Freeze Dryer (Ilshin Lab Co. Ltd., South Korea) in a vacuum of 5 mTorr for 48 hrs, in which the shelf temperature was raised to 40° C., while the condenser temperature remained at −70° C.

1-3. Preparation of GGEx0014

Crude herbs of Thallus Laminariae seu Eckloniae were ground to a size of 200 mesh. 500 g of the powder and 5000 cc of water were added to an electronic herbal extractor, boiled at 95° C. for 22 hrs, and filtered. The filtrate was freeze-dried in an Ilshin Programmable Freeze Dryer (Ilshin Lab Co. Ltd., South Korea) in a vacuum of 5 mTorr for 48 hrs, in which the shelf temperature was raised to 40° C., while the condenser temperature remained at −70° C.

1-4. Preparation of GGEx0015

Crude herbs of Herba Ephedrae and Radix et Rhizoma Rhei were individually ground to a size of 200 mesh. The Herba Ephedrae powder was boiled in ten volumes of water at 95° C. for 21 hrs and 50 min. The powder of Radix et Rhizoma Rhei was immersed in ten volumes of water for 21 hrs and 50 min. Then, the Herba Ephedrae solution was mixed with the immersion solution of Radix et Rhizoma Rhei at a ratio of 1:1 (50%:50%), and boiled for an additional 10 min. After a total of 22 hrs of boiling in water, the boiled mixture was filtrated. The filtrate was freeze-dried in an Ilshin Programmable Freeze Dryer (Ilshin Lab Co. Ltd., South Korea) in a vacuum of 5 mTorr for 48 hrs, in which the shelf temperature was raised to 40° C., while the condenser temperature remained at −70° C.

1-5. Preparation of GGEx0016

Crude herbs of Herba Ephedrae and Thallus Laminariae seu Eckloniae were individually ground to a size of 200 mesh, and mixed at a ratio of 4:6 (40%:60%). The mixture was mixed with ten volumes of water at 95° C. for 22 hrs, and filtered. The filtrate was freeze-dried in an Ilshin Programmable Freeze Dryer (Ilshin Lab Co. Ltd., South Korea) in a vacuum of 5 mTorr for 48 hrs, in which the shelf temperature was raised to 40° C., while the condenser temperature remained at −70° C.

1-6. Preparation of GGEx0017

Crude herbs of Radix et Rhizoma Rhei and Thallus Laminariae seu Eckloniae were individually ground to a size of 200 mesh. The powder of Radix et Rhizoma Rhei was immersed in ten volumes of water for 21 hrs and 50 min. The powder of Thallus Laminariae seu Eckloniae was boiled in ten volumes of water at 95° C. for 21 hrs and 50 min, then mixed with the immersion solution of Radix et Rhizoma Rhei at a ratio of 1:1 (50%:50%), and boiled for an additional 10 min. After a total of 22 hrs of boiling in water, the boiled mixture was filtrated. The filtrate was freeze-dried in an Ilshin Programmable Freeze Dryer (Ilshin Lab Co. Ltd., South Korea) in a vacuum of 5 mTorr for 48 hrs, in which the shelf temperature was raised to 40° C., while the condenser temperature remained at −70° C.

1-7. Preparation of GGEx0018

Crude herbs of Herba Ephedrae, Thallus Laminariae seu Eckloniae and Radix et Rhizoma Rhei were individually ground to a size of 200 mesh. The three herbal powders thus obtained were used at a ratio of 4:3:3 (40%:30%:30%). First, the powders of Herba Ephedrae and Thallus Laminariae seu Eckloniae were mixed and boiled in ten volumes of water at 95° C. for 21 hrs and 50 min. The powder of Radix et Rhizoma Rhei was immersed in ten volumes of water for 21 hrs and 50 min. Then, the boiled solution of Herba Ephedrae and Thallus Laminariae seu Eckloniae was mixed with the immersion solution of Radix et Rhizoma Rhei, and boiled for an additional 10 min. The final solution was filtered. The filtrate was freeze-dried in an Ilshin Programmable Freeze Dryer (Ilshin Lab Co. Ltd., South Korea) in a vacuum of 5 mTorr for 48 hrs, in which the shelf temperature was raised to 40° C., while the condenser temperature remained at −70° C.

1-8. Preparation of Reductil® as a Comparative Control

Sibutramine, which is an FDA-approved obesity drug, was purchased from Abbot Korea Ltd., and used as a Western medicine control.

Example 2

Evaluation of Effects on Body Weight in Animals 2-1. Preparation of Experimental Animal Five male C57BL/6J mice and forty five male ob/ob mice, which were 9 weeks old, were purchased from Central Lab.

Animal Inc. (Seoul, South Korea). The mice were grouped randomly, and each group was composed of five mice.

Mice were housed in a controlled chamber at 21±2° C. under a relative humidity of 55±5%, air ventilation of 15-17 times/hour and a light intensity of 150-300 Lux with a 12-hour light/dark cycle (turned on at 06:00, turned off at 18:00). All animals were maintained under specific pathogen free (SPF) conditions, and were allowed free access to feed and water.

2-2. Preparation of Test Groups and Drug Administration

Each test group was composed of five male mice, and named according to the administered drug. That is, the GGEx0012 preparation was administered at a dose of 1217 mg/kg/day (GGEx0012 treatment group). Similarly, the GGEx0013 preparation was administered at a dose of 1217 mg/kg/day (GGEx0013 treatment group), the GGEx0014 preparation at a dose of 1217 mg/kg/day (GGEx0014 treatment group), the GGEx0015 preparation at a dose of 1217 mg/kg/day (GGEx0015 treatment group), the GGEx0016 preparation at a dose of 1217 mg/kg/day (GGEx0016 treatment group), the GGEx0017 preparation at a dose of 1217 mg/kg/day (GGEx0017 treatment group), and the GGEx0018 preparation at a dose of 1217 mg/kg/day (GGEx0018 treatment group). Reductil® was administered at a dose of 2.5 mg/kg/day (Reductil treatment group). The administration was carried out for a test period of 11 weeks (Table 1). As controls, C57BL/6J and ob/ob-vehicle groups were fed with a general feedstuff.

TABLE 1

| | Group | Mice No. | Sex | Dose (mg/kg BW) |
|---|---|---|---|---|
| | C57BL/6J | 5 | Male | 0 |
| Ob/ob | Vehicle | 5 | Male | 0 |
| | GGEx0012 | 5 | Male | 1217 mg/kg |
| | GGEx0013 | 5 | Male | 1217 mg/kg |
| | GGEx0014 | 5 | Male | 1217 mg/kg |
| | GGEx0015 | 5 | Male | 1217 mg/kg |
| | GGEx0016 | 5 | Male | 1217 mg/kg |
| | GGEx0017 | 5 | Male | 1217 mg/kg |
| | GGEx0018 | 5 | Male | 1217 mg/kg |
| | Reductil | 5 | Male | 2.5 mg/10 ml |

2-3. Evaluation of Effects on Body Weight

Figure 1:
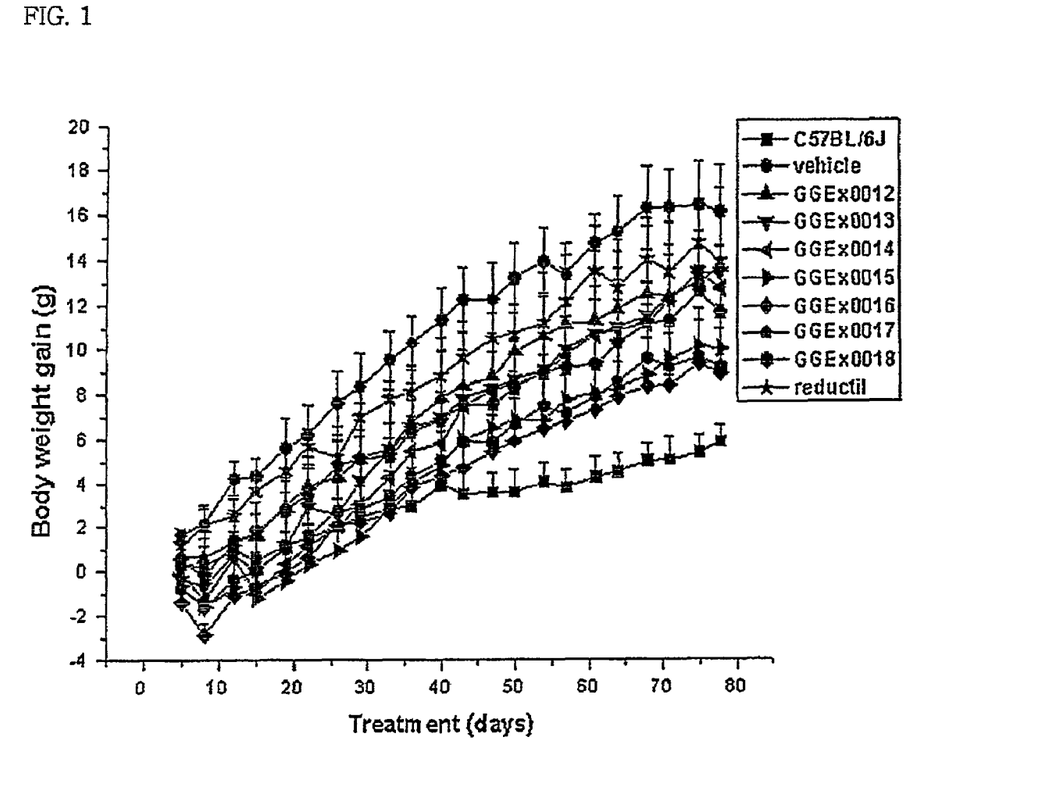
FIG. 1 is a graph showing the body weight (BW) gains of control obese mice and mice dosed with GGEx0012, GGEx0013, GGEx0014, GGEx0015, GGEx0017 and Reductil® over time.

FIGS. 1 and 2 show the body weight (BW) gain of each test group over time. As shown in FIGS. 1 and 2, the GGEx0016 treatment resulted in a statistically significant decrease in weight gain compared to the obesity control (vehicle), GGEx0012, GGEx0013, GGEx0014, GGEx0015 and GGEx0017 treatment, and Reductil® treatment as a comparative control. Such a decrease in weight gain was found to be remarkable compared to the cases in which mice were dosed with a vehicle, GGEx0013, GGEx0014, GGEx0017 and Reductil®. Also, there was no significant difference in weight gain between the GGEx0018 and GGEx0016 treatment groups. These results indicated that the GGEx0016 and GGEx0018 preparations, prepared in Examples 1-5 and 1-7, respectively, have anti-obesity effects superior to those of the control groups and other treatment groups.

2-4. Evaluation of Feeding Efficiency Ratio

The feeding efficiency ratio was calculated based on the results of Example 2-3 according to Equation 1, below, and is presented as a graph in FIG. 3.

$$\text{Feeding efficiency ratio}(FER)(\%) = \frac{\text{body weight gain(g)}}{\text{feed intaking(g)}} \quad \text{[Equation 1]}$$

A small increase in weight gain despite a large feed intake means that a drug has an effect of suppressing weight gain. Thus, the feeding efficiency ratio is an indicator of obesity. When the feeding efficiency ratio is decreased, a drug has an anti-obesity effect.

As shown in FIG. 3, the GGEx0016 treatment group displayed a FER lower than those of the obesity control (vehicle), GGEx0012, GGEx0013, GGEx0014, GGEx0015, GGEx0017 and Reductil® groups. In particular, a statistically significant increase in feeding efficiency was observed in mice dosed with a vehicle (obesity control), GGEx0012, GGEx0013 and Reductil®. Also, no statistically significant difference in FER was seen between the GGEx0018 and GGEx0016 treatment groups. These results indicated that the GGEx0016 and GGEx0018 preparations prepared in Examples 1-5 and 1-7, respectively, which remarkably reduced FER of mice compared to the control and other GGEx preparations, have high anti-obesity effects.

Example 3

Biochemical Analysis of Mouse Blood Samples

Figure 4:
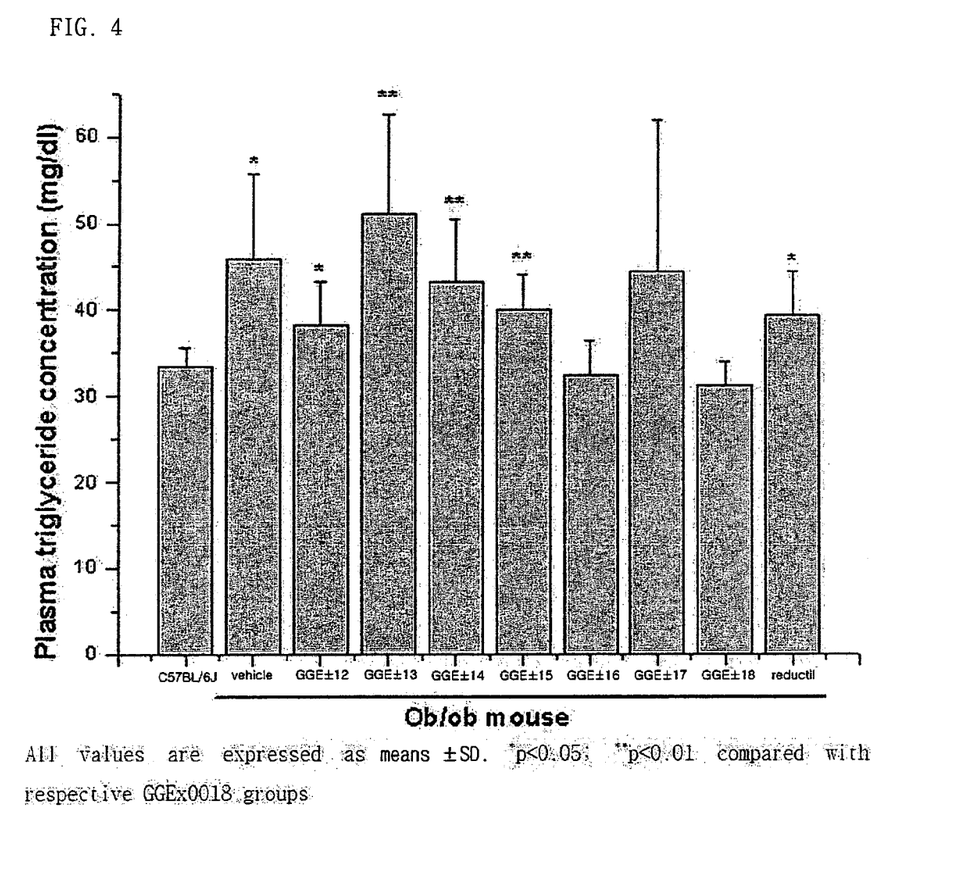
FIG. 4 is a graph showing the plasma triglyceride levels of control obese mice and mice dosed with GGEx0012, GGEx0013, GGEx0014, GGEx0015, GGEx0017 and Reductil®.
Figure 5:
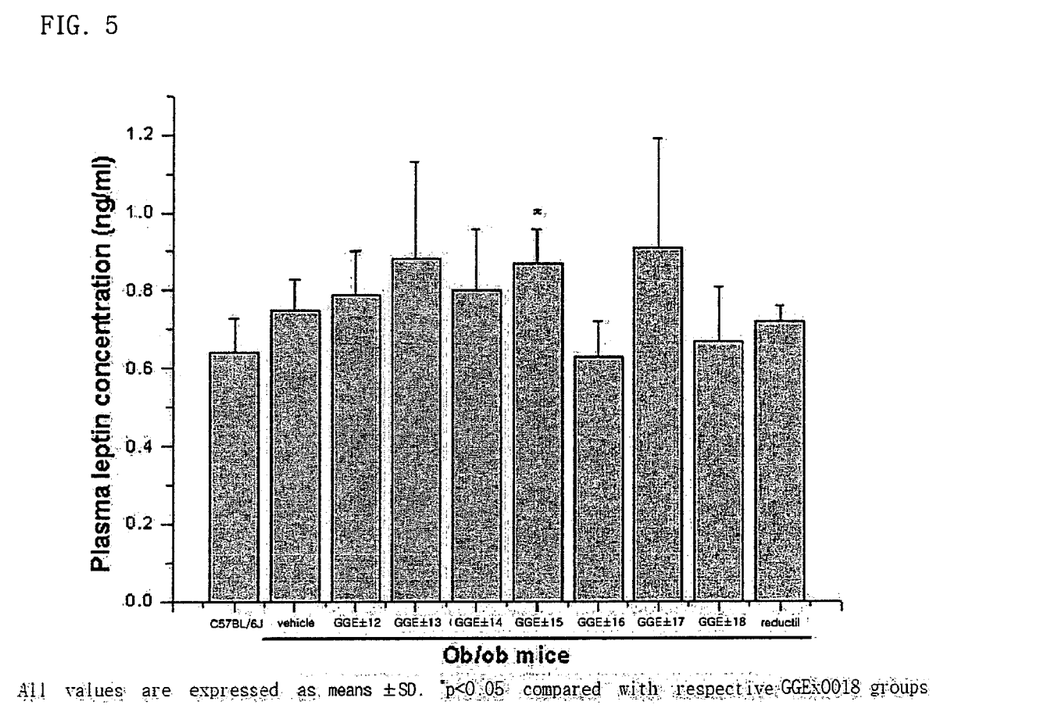
FIG. 5 is a graph showing the plasma leptin levels of control obese mice and mice dosed with GGEx0012, GGEx0013, GGEx0014, GGEx0015, GGEx0017 and Reductil®.
Figure 6:
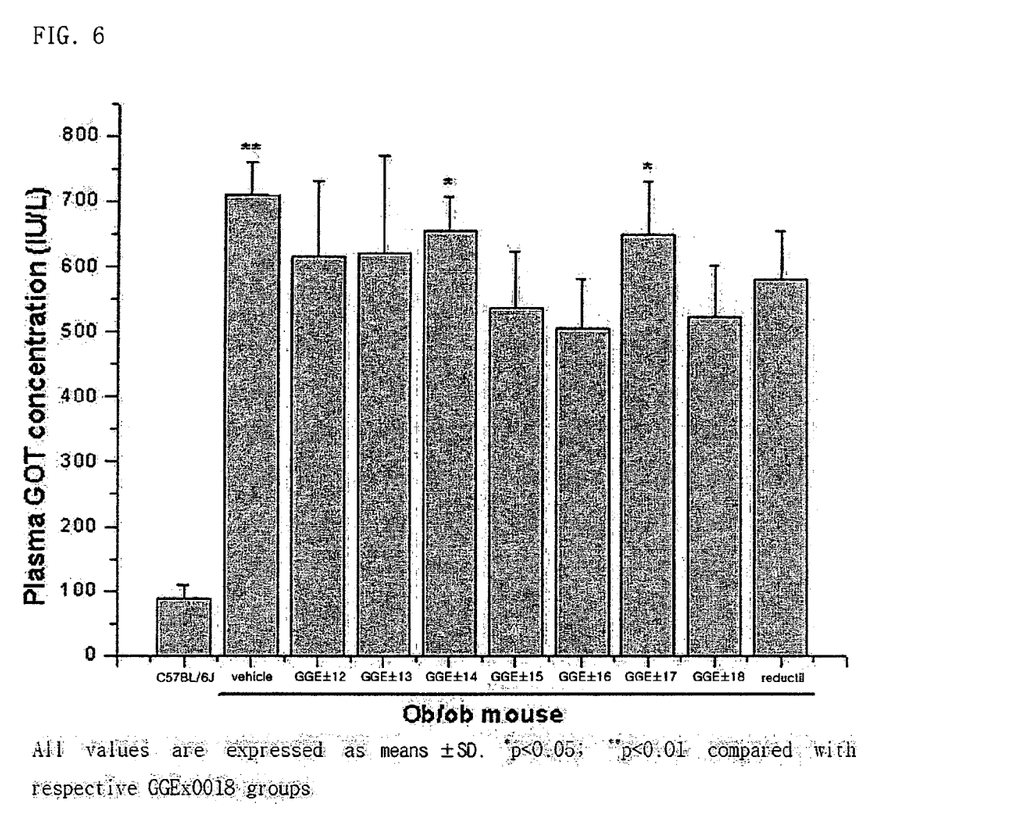
FIG. 6 is a graph showing the plasma glutamic oxaloacetic transaminase (GOT) levels of control obese mice and mice dosed with GGEx0012, GGEx0013, GGEx0014, GGEx0015, GGEx0017 and Reductil®.

For the biochemical analysis of mouse blood samples, mice were starved for 12 hrs, and anesthetized with diethyl ether. Through a middle abdominal incision, 5 ml blood samples were collected from the saphenous vein and allowed to coagulate for about 10 min at room temperature using a plasma separation tube (Gel and Clot Activator Tube (5 ml), IMPROVE, Germany). Then, the blood samples were centrifuged for 15 min at 3,500 rpm using a high-speed refrigerated centrifuge (HSL-05A, Hanil, Japan). The separated plasma was stored at −4° C. until use. Plasma concentrations of triglyceride (TG), leptin and glutamic oxaloacetic transaminase (GOT) were determined using a blood biochemical analyzer (Clima plus, RAL, USA). The results are shown in FIGS. 4 to 6.

The blood triglyceride level is typically higher in obese groups than in non-obese groups. As shown in FIG. 4, the GGEx0016 treatment group exhibited lower plasma triglyceride levels than those of the obesity control (vehicle), GGEx0012, GGEx0013, GGEx0014, GGEx0015 and Reductil® groups. In particular, the obesity control (vehicle), GGEx0012, GGEx0013, GGEx0014, GGEx0015 and Reductil® groups displayed statistically significantly higher triglyceride levels than other groups. Also, no statistically significant difference in plasma triglyceride level was seen between the GGEx0018 and GGEx0016 treatment groups.

The blood leptin level is typically higher in obese groups than in non-obese groups. As shown in FIG. 5, the GGEx0016 treatment group exhibited lower plasma leptin levels than those of the obesity control (vehicle), GGEx0012, GGEx0013, GGEx0014, GGEx0015, GGEx0017 and Reductil® groups. In particular, the GGEx0015 treatment group displayed statistically significantly higher plasma leptin levels than the other groups. Also, no statistically significant difference in plasma leptin level was seen between the GGEx0018 and GGEx0016 treatment groups.

The plasma activity of glutamic oxaloacetic transaminase (GOT) is generally used as an important marker in the diagnosis of hepatotoxicity and heart diseases. When hepatic tissues are disrupted, fatty substances accumulate on the inner lining of coronary arteries. The resulting blockage of coronary arteries causes locally severe insufficient oxygen supply, leading to regional degeneration of myocardial tissues. This process is called myocardial infarction. Damaged myocardial cells secrete an aminotransferase enzyme, which increases the amount of GOT in plasma.

As shown in FIG. 6, the GGEx0016 treatment group exhibited lower plasma GOT levels than those of the obesity control (vehicle), GGEx0012, GGEx0013, GGEx0014, GGEx0015, GGEx0017 and Reductil® groups. In particular, the obesity control (vehicle), GGEx0014 and GGEx0017 groups displayed statistically significantly higher plasma GOT levels than the other groups. Also, no statistically significant difference in plasma GOT level was seen between the GGEx0018 and GGEx0016 treatment groups.

Example 4

Evaluation of Effects on Fat Accumulation in Liver Tissues

After blood samples were collected in Example 3, liver tissues were excised from mice. The excised liver tissues were fixed in 10% phosphate-buffered formalin for over one day, and washed with running water for over 12 hrs to remove formalin. Then, the tissues were dehydrated using a graded series of ethanol: 60%, 70%, 80%, 90%, 95% and 100% for 1 hr each. The dehydrated tissues were cleared in xylene three times for 1 hr each, and embedded in paraffin twice for 1 hr each time. The paraffin tissues were cut into sections about 3 μm thick. The sections were placed on glass slides, dried, and stained with hematoxylin-eosin. For permanent preservation of the tissue sections, after water on the slides was removed, a mounting medium (Sigma, Mo., USA) was dropped on the tissue sections. A coverslip was carefully placed on the drop avoiding the formation of air bubbles around the tissue section and coverslip. Tissue sections were photographed and analyzed to determine the volume of fat deposits using an image analysis system (Image pro-plus, MD, USA).

Figure 7:
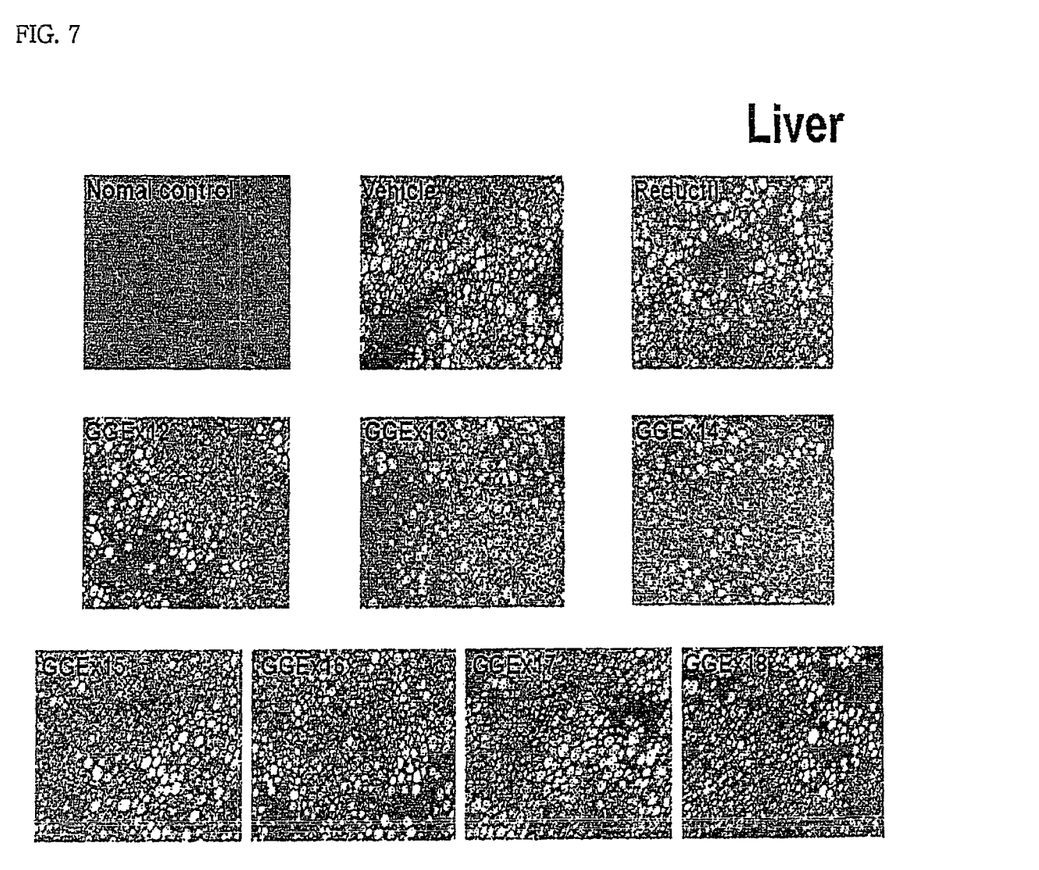
FIG. 7 photographically shows the lipid accumulation in liver tissues of control obese mice and mice dosed with GGEx0012, GGEx0013, GGEx0014, GGEx0015, GGEx0017 and Reductil®.
Figure 8:
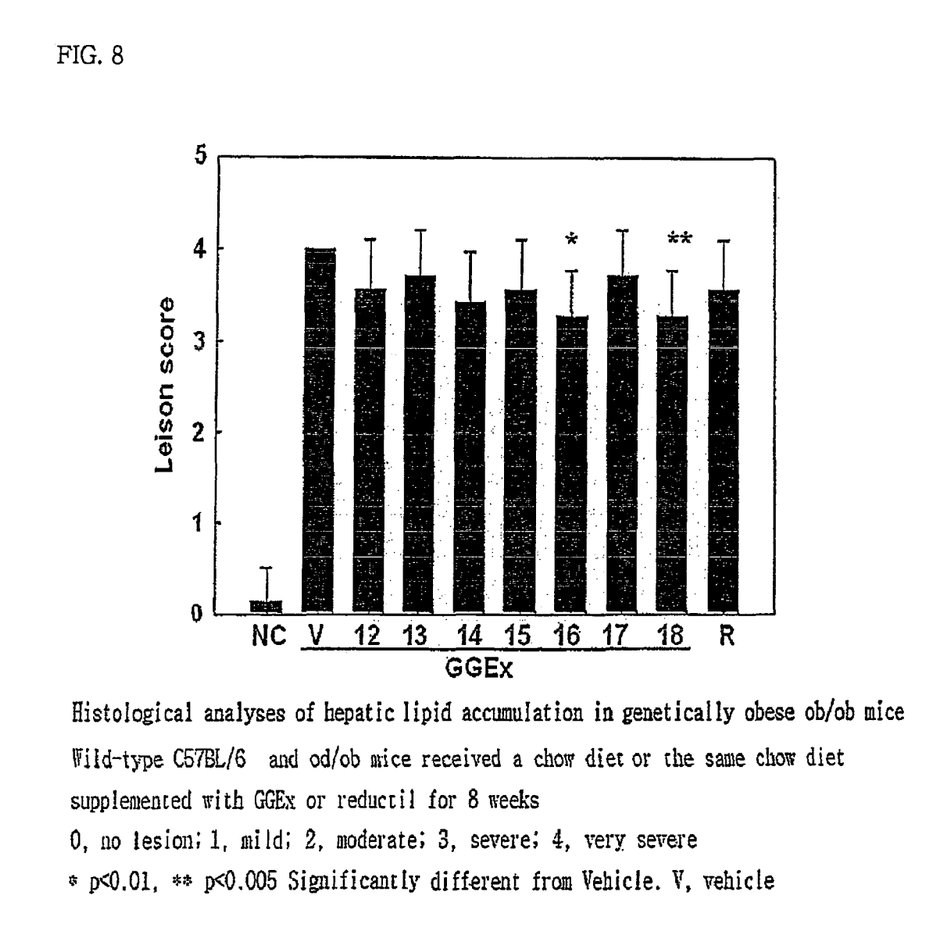
FIG. 8 is a graph expressing numerically the hepatic lipid accumulation of control obese mice and mice dosed with GGEx0012, GGEx0013, GGEx0014, GGEx0015, GGEx0017 and Reductil®.

As shown in FIGS. 7 and 8, when genetically obese ob/ob mice having fatty livers in which a great amount of fat was accumulated were dosed with GGEx0013, GGEx0014, GGEx0016 and GGEx0018 preparations, they exhibited decreased lipid accumulation in the liver. In particular, the hepatic lipid accumulation was more effectively suppressed in GGEx0016 ($p<0.001$) and GGEx0018 ($p<0.0005$) treatment groups.

Example 5

Evaluation of Acute Toxicity of the Present Compositions Upon Oral Administration to Rats An acute toxicity test was carried out using 6 week-old specific pathogen-free (SPF) SD rats. The GGEx0016 and GGEx0018 preparations were suspended in a 0.5% methylcellulose solution and administered orally to groups each consisting of two rats at a single dose of 1 g/kg/ml. After the GGEx preparations were administered, death, clinical symptoms and body weight change were observed, and a hematological test and hematobiochemical analysis were performed. Upon autopsy, abnormalities in abdominal organs and chest organs were visually observed.

As a result, all rats administered with the GGEx preparations exhibited no particular clinical symptoms, no death, no change in weight, and no toxicity upon the hematological assay, hematobiochemical analysis and autopsy. Taken together, the present compositions exhibited no toxicity even at a dose of 1 g/kg in all rats and had a 50% lethal dose (LD50) upon oral administration in amounts greater than 1 g/kg. These results indicated that the present compositions are safe.

Hereinafter, formulation or processing of the present compositions will be exemplified.

Formulation Example 1

Preparation of Pharmaceutical Formulations

1. Preparation of Powder

| | |
|---|---|
| GGEx0016 or GGEx0018 | 2 g |
| Lactose | 1 g |

The above ingredients were mixed and packaged in plastic bags.

2. Preparation of Tablets

| | |
|---|---|
| GGEx0016 or GGEx0018 | 100 mg |
| Corn starch | 100 mg |
| Lactose | 100 mg |
| Magnesium stearic acid | 2 mg |

The above ingredients were mixed and tabletted according to a conventional method to obtain tablets.

3. Preparation of Capsules

| | |
|---|---|
| GGEx0016 or GGEx0018 | 100 mg |
| Corn starch | 100 mg |
| Lactose | 100 mg |
| Magnesium stearic acid | 2 mg |

The above ingredients were mixed and loaded into gelatin capsules according to a conventional capsule preparation method.

Formulation Example 2

Preparation of Food

The Gyeongshin-gangjee-hwan (GGEx) preparations of the present invention were used as food additives, as follows.

1. Preparation of Cooking Sauce

A cooking sauce for suppressing obesity was prepared using GGEx0016 or GGEx0018 in an amount of 20% to 95% by weight.

2. Preparation of Tomato Ketchup and Other Tomato Sauces

A tomato ketchup or sauce for suppressing obesity was prepared by adding 0.2 to 1.0 wt % of GGEx0016 or GGEx0018 to a conventional tomato ketchup or sauce.

3. Preparation of Flour Products 0.5 to 5.0 wt % of GGEx0016 or GGEx0018 was added to wheat flour and used for making breads, cakes, cookies, crackers, and noodles, thereby creating flour products for suppressing obesity.

4. Preparation of Soups and Gravies 0.1 to 5.0 wt % of GGEx0016 or GGEx0018 was added to a conventional soup and gravy, thereby creating meat products, noodle soups and gravies for suppressing obesity.

5. Preparation of Ground Beef 10 wt % of GGEx0016 or GGEx0018 was added to conventional ground beef, thereby creating ground beef for suppressing obesity.

6. Preparation of Dairy Products 5 to 10 wt % of GGEx0016 or GGEx0018 was added to milk, and the milk was used to make butter, ice cream, and other products, thereby creating various dairy products for suppressing obesity.

7. Preparation of Health Grain Powder

Brown rice, barley, glutinous rice and adlay were pregelatinized using a known method, dried, distributed, and pulverized to a particle size of 60 mesh using a pulverizer.

Black beans, black sesame seeds and wild sesame seeds were steamed using a known method, dried, distributed, and pulverized to a particle size of 60 mesh using a pulverizer.

GGEx0016 or GGEx0018 was concentrated under pressure using a vacuum concentrator, spray-dried or dried using a hot air dryer, and pulverized to a particle size of 60 mesh using a pulverizer.

The powders of grains, seeds and GGEx0016 or GGEx0018 thus obtained were mixed at the following ratio.

Grains: 30 wt % of brown rice, 15 wt % of adlay, 20 wt % of barley
Seeds: 8 wt % of black beans, 7 wt % of wild sesame, 7 wt % of black sesame
GGEx0016 or GGEx0018 powder: 3 wt %
Reishi mushroom: 0.5 wt %
Rehmanniae Radix: 0.5 wt %

Formulation Example 3

Preparation of Beverages

1. Preparation of Carbonated Beverages 5-10% of sucrose, 0.05-0.3% of citric acid, 0.005-0.2% of caramel, and 0.1-1% of vitamin C were pooled and mixed with 79-94% of purified water to generate a syrup. The syrup was pasteurized at 85-98° C. for 20-180 sec, and mixed with cold water at a ratio of 1:4. 5 g of GGEx0016 or GGEx0018 was added to the syrup. Then, 0.5-0.82% of carbonic acid gas was pushed into the liquid, thereby yielding a carbonated beverage containing the GGEx0016 or GGEx0018 preparation according to the present invention.

2. Preparation of Health Drinks

GGEx0016 or GGEx0018 was homogeneously mixed with liquid fructose (0.5%), oligosugar (2%), sucrose (2%), edible salt (0.5%) and water (75%), pasteurized for a short time, and placed in a small-size container, such as a glass bottle or a PET bottle, thereby yielding a health drink.

3. Preparation of Vegetable Juices 5 g of GGEx0016 or GGEx0018 was added to 1,000 ml of a tomato or carrot juice, thereby yielding a vegetable juice for suppressing obesity.

4. Preparation of Fruit Juices 1 g of GGEx0016 or GGEx0018 was added to 1,000 ml of apple or grape juice, thereby yielding a fruit juice for suppressing obesity.

INDUSTRIAL APPLICABILITY

As described hereinbefore, the present compositions are superior in promoting weight loss and reducing adipose tissues when compared to conventional anti-obesity compositions, such as Reductil®, which has been known to have an anti-obesity effect.

The invention claimed is:

1. A pharmaceutical composition for suppressing obesity consisting of Herba Ephedrae, Thallus Laminariae seu Eckloniae and Radix et Rhizoma Rhei mixed at ratio of 10-50:20-50:20-50 weight percent based on weight of crude herbs.

2. A health food composition for suppressing obesity consisting of Herba Ephedrae, Thallus Laminariae seu Eckloniae and Radix et Rhizoma Rhei mixed at ratio of 10-50:20-50:20-50 weight percent based on weight of crude herbs.

* * * * *

UNITED STATES PATENT AND TRADEMARK OFFICE
CERTIFICATE OF CORRECTION

PATENT NO. : 8,404,282 B2  Page 1 of 1
APPLICATION NO. : 12/596018
DATED : March 26, 2013
INVENTOR(S) : Jung et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 520 days.

Signed and Sealed this
First Day of September, 2015

Michelle K. Lee
*Director of the United States Patent and Trademark Office*